United States Patent [19]
Kawabe et al.

[11] Patent Number: 5,763,691
[45] Date of Patent: Jun. 9, 1998

[54] ETHYLENE GLYCOL PROCESS

[75] Inventors: Kazuki Kawabe, Yokkaichi; Kazuhiko Murata, deceased, late of Tokyo, by Reiji Murata, Keiko Murata, heirs; Toshiyuki Furuya, Yokkaichi, all of Japan

[73] Assignee: Mitsubishi Chemical Corporation, Tokyo, Japan

[21] Appl. No.: 756,800

[22] Filed: Nov. 26, 1996

[30] Foreign Application Priority Data

Nov. 30, 1995 [JP] Japan ................. 7-312631

[51] Int. Cl.⁶ ........................................ C07C 27/00
[52] U.S. Cl. .............................. 568/867; 568/858
[58] Field of Search .................... 568/867; 11/858

[56] References Cited

U.S. PATENT DOCUMENTS

| | | | |
|---|---|---|---|
| 4,160,116 | 7/1979 | Mieno et al. | 568/867 |
| 4,233,221 | 11/1980 | Raines et al. | 260/340.2 |
| 4,508,927 | 4/1985 | Bhise et al. | |

FOREIGN PATENT DOCUMENTS 2 107 712  5/1983  United Kingdom.

OTHER PUBLICATIONS

*Patent Absracts of Japan*, 9(197) (C–128), Oct. 6, 1982 (abstract of JP 57–106631).

*Patent Abstract of Japan*, 8(98) (C–221), May 9, 1984 (abstract of JP 59–013741).

*Primary Examiner*—Porfirio Nazario-Gonzalez
*Assistant Examiner*—Karl J. Puttlitz
*Attorney, Agent, or Firm*—Wenderoth, Lind & Ponack, L.L.P.

[57] ABSTRACT

The present invention relates to a process for producing ethylene glycol from ethylene oxide wherein ethylene oxide in a gas resulting from oxidation of ethylene is absorbed in a specific absorbing solution, is allowed to react with carbon dioxide, converted into ethylene carbonate, and then subjected to hydrolysis to produce ethylene glycol.

According to the present invention, a large energy consuming step such as stripping of ethylene oxide and separation of excess amounts of water during the ethylene glycol production becomes unnecessary and the process can be greatly simplified by combining the ethylene oxide absorption step and the carbonation step.

9 Claims, 1 Drawing Sheet

ETHYLENE GLYCOL PROCESS

BACKGROUND OF THE INVENTION

1. Field of the Invention

The present invention relates to a process for producing ethylene glycol from ethylene oxide. In particular, it relates to a process for producing ethylene glycol wherein ethylene oxide in a gas resulting from oxidation of ethylene is absorbed in a specific absorbing solution, is then allowed to react with carbon dioxide, to be converted into ethylene carbonate, and then subjected to hydrolysis to produce ethylene glycol.

The ethylene glycol is used as a raw material for producing a polyester or polyurethane type polymer or as antifreeze for engines and the like.

2. Description of the Related Art

The preparation of monoethylene glycol (hereinafter simply abbreviated as ethylene glycol) from ethylene through ethylene oxide comprises the following steps.

First, ethylene is converted into ethylene oxide by vapor phase catalytic oxidation using oxygen in the presence of a silver catalyst. The gas resulting from the oxidation usually contains ethylene oxide in an amount of 0.5–5 mol %. The gas containing ethylene oxide is contacted with a large amount of water so that the ethylene oxide contained in the gas resulting from the oxidation is absorbed in the water and the ethylene oxide is recovered in the form of an aqueous solution. Then the obtained diluted aqueous solution of ethylene oxide (the concentration of the ethylene oxide is usually 1–5 mol %) is heated under reduced pressure so that the ethylene oxide in the aqueous solution is stripped and separated, and the ethylene oxide is recovered from the top of the column. The water remaining after removing the ethylene oxide is cooled, and recycled to the absorbing step.

Ethylene oxide is isolated from the mixture mainly containing ethylene oxide and water obtained by the stripping treatment, if necessary, then water in an amount in excess of that normally used for the ethylene oxide is added (water is usually in an amount of 10–25 moles for each mole of ethylene oxide) and ethylene glycol is obtained by hydration reaction. In the hydration reaction of ethylene oxide, unreacted ethylene oxide and produced ethylene glycol are allowed to react successively, and in addition to the ethylene glycol, diethylene glycol, triethylene glycol and other higher polyethylene glycols are produced as by-products. Accordingly, after the completion of the hydration reaction, the product can only be obtained after sequentially separating these glycols by such procedures as distillation.

As mentioned above, the ethylene glycol production according to the prior art requires both an ethylene oxide isolation process comprising absorbing and stripping systems, and an ethylene glycol production process comprising an ethylene oxide hydration reaction system and a glycol separation purification system.

However, the conventional process has such deficiencies that it not only needs a large number of steps for obtaining ethylene glycol as a product, but also consumes a lot of energy, as described below, in order to produce the ethylene glycol.

First, the procedure of stripping and separating ethylene oxide absorbed in the absorbing solution consumes a lot of energy.

As mentioned above, in order to carry out absorption and separation of ethylene oxide without substantial loss, from the gas obtained by oxidation, absorption water in an amount sufficiently large enough for the gas used is required. After the absorption/separation procedure of the ethylene oxide, a large amount of this absorption water must then be heated, usually up to 100°–150° C. in the process for stripping and separating ethylene, thereby requiring a large amount of heat energy. Further, as more than small amounts of the absorption water is evaporated, even more energy is required.

There is also a method proposed in U.S. Pat. No. 4,273,221, in which ethylene carbonate is used instead of water, as an absorbing solution for ethylene oxide. According to this process, the amount of heat energy necessary for elevating the temperature to the level required for the stripping procedure can be decreased, since the specific heat of the ethylene carbonate is less than half of that of water. However, since the melting point of ethylene carbonate is as high as 39° C., the operation temperature of the absorption column cannot be lowered sufficiently, and the absorption loss of the ethylene oxide is more than a little. Also, since the stripping procedure itself is not eliminated even though the heat energy required is decreased, the problem still remains.

Second, as the hydration reaction is carried out under largely excess conditions, the separation of the excess water after the hydration reaction requires a large amount of energy for the following reasons. The selectivity of ethylene oxide to ethylene glycol, diethylene glycol, and triethylene glycol is determined by the ratio of the ethylene oxide to water supplied to the hydration reactor. The larger the ratio of water to the ethylene oxide, the higher the selectivity of ethylene glycol becomes.

Generally, among ethylene glycols, diethylene glycol, triethylene glycol or higher polyglycols, they have a narrower range of application than that of the ethylene glycol. Accordingly, in order to raise the selectivity of ethylene oxide to the ethylene glycol which is in great demand, an excess amount of water, i.e. 10–25 times the molar quantity of ethylene oxide, is often supplied for hydration reaction as described above. Therefore, the concentration of the ethylene glycol obtained after completion of the reaction is at most around 10–20% by weight.

In the recovery and the purification process of the ethylene glycol, this excess amount of water must be removed by a distillation procedure from the mixture of ethylene glycol and water, and that requires a large amount of energy. For example, when water in a molar quantity 20 times that of ethylene oxide is supplied, the heat necessary for removing by evaporation the unused water in a molar quantity about 19 times that of ethylene glycol, is 170 kcal per mole of ethylene glycol. That means about 5.5 tons of steam is consumed for 1 ton of ethylene glycol. Therefore, in order to further improve the selectivity of ethylene glycol, the ratio of water used must be raised more, which increases the amount of water to be removed by evaporation, so that a larger amount of energy is required.

Processes have also been proposed to decrease the amount of water for ethylene oxide but to keep the selectivity for ethylene glycol at a high level, in which isolated ethylene oxide is allowed to react with carbon dioxide to produce ethylene carbonate, which is then hydrolyzed to produce ethylene glycol with high selectivity. For example, in a process proposed in Japanese Patent Publication No. 3-23548, ethylene oxide is converted to ethylene carbonate in the presence of a halogenated organic quaternary phosphonium salt, and in a process proposed in Japanese Patent Publication No. 4-27972, the resulting ethylene carbonate is subjected to hydrolysis using the same catalyst to give high purity ethylene glycol. There is also another process proposed in Japanese Patent Laid-open No. 57-106631 in which ethylene oxide is converted to ethylene carbonate using a halide of an alkali metal, followed by hydrolysis.

According to these processes, it is not necessary to supply water to the reactor in amounts more than is to be consumed by the reaction in order to achieve high selectivity, and as a result the second drawback, i.e. the large amount of energy required for removing the excess amount of water by distillation procedures, can be avoided. However, in all of these processes, isolated ethylene oxide is used as the starting material, and there have been no proposals on absorption procedures or stripping procedures for recovering, concentrating and isolating the ethylene oxide from the gas resulting from oxidation. For recovering ethylene oxide from the gas containing ethylene oxide according to the conventional process, a stripping procedure is required as mentioned above, and the first drawback, i.e. the large amount of energy required, remains unimproved. The whole process from the oxidation of ethylene to the purification of ethylene glycol is very long and the construction costs are high. This disadvantageously leads to an increase in the ethylene glycol production costs.

SUMMARY OF THE INVENTION

As a result of intensive research to solve the above-mentioned problems, the present inventors have discovered a process in which ethylene oxide is separated from a gas resulting from oxidation reaction, and ethylene glycol can be advantageously produced in a simplified and low-energy process, to complete the present invention.

According to the present invention, there is provided a process for producing ethylene glycol from ethylene oxide, comprising;

step (1): a step in which ethylene oxide in a gas resulting from oxidation of ethylene is absorbed in an absorbing solution mainly containing ethylene carbonate and ethylene glycol, step (2): a step in which ethylene oxide in the absorbing solution is allowed to react with carbon dioxide in the presence of a carbonation catalyst, step (3): a step in which a part of ethylene carbonate resulting in the absorbing solution is subjected to hydrolysis in the presence of a hydrolytic catalyst and the remaining ethylene carbonate is allowed to recycle as an absorbing solution, and step (4): a step in which ethylene glycol is recovered from the hydrolysate by distillation.

The features of the present invention are as follows. First, a mixed solvent mainly containing ethylene glycol and ethylene carbonate is used as an ethylene oxide absorbing solution. Second, the ethylene oxide is absorbed and separated from the gas containing ethylene oxide using the absorbing solution, then without stripping and separating the ethylene oxide, the absorbing solution is directly used as a reactor feed, and the ethylene oxide in the absorbing solution is converted into ethylene carbonate. Third, the major portion of the solution resulting from the carbonation reaction is recycled to the absorbing operation as an absorbing solution. Fourth, a part of the solution resulting from the carbonation reaction is drawn out and ethylene carbonate in the solution is hydrolyzed by adding a much smaller amount of water than that used conventionally in order to carry out selective and low-energy production of ethylene glycol.

DESCRIPTION OF THE PREFERRED EMBODIMENT

Figure 1:
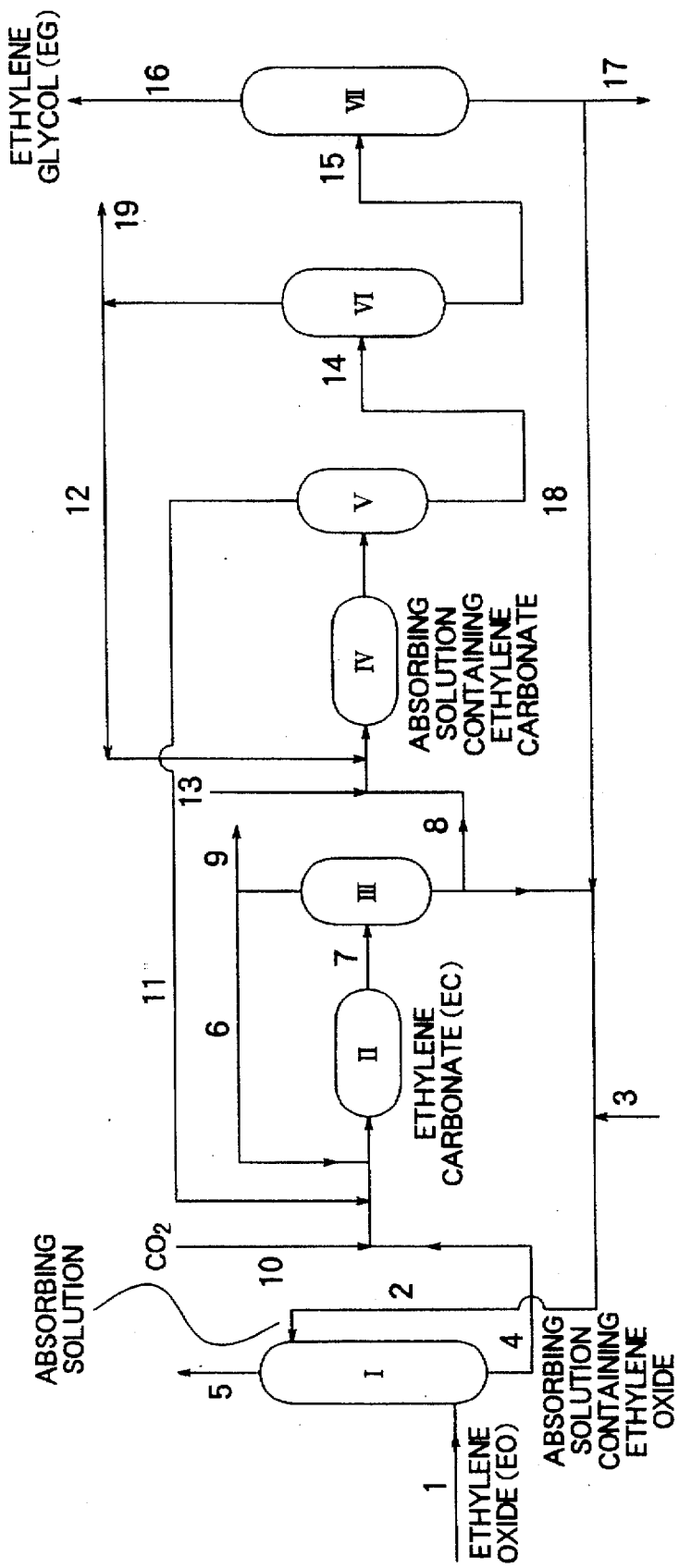
FIG. 1 is a flow diagram of an embodiment of the present invention.

One example of the embodiment of the present invention will be described in detail with reference to FIG. 1.
(Absorption step of ethylene oxide (Step 1))

Absorption of ethylene oxide is carried out in an absorption apparatus I by contacting a gas supplied via line 1 which results from a oxidation reaction and contains ethylene oxide, with an absorbing solution supplied via line 2.

The gas resulting from the oxidation reaction and containing ethylene oxide is usually obtained by catalytic vapor phase oxidation of ethylene over a silver catalyst, and contains ethylene oxide usually in an amount of 0.5–5 mol %. In addition to that, it contains oxygen, ethylene, generated water, carbon dioxide, nitrogen, methane, ethane and trace amounts of aldehydes. The gas containing ethylene oxide is desirably cooled by a heat-exchanger and the like usually to 10°–80°0 C., preferably 30°–60° C., before it is supplied to the absorption apparatus.

The main components of the absorbing solution are ethylene carbonate and ethylene glycol. Ethylene carbonate and ethylene glycol usually comprise 50% by weight or more of the whole absorbing solution. The weight ratio of the ethylene glycol to ethylene carbonate is usually 0.1–9, preferably 0.3–4. As an optional component except for the ethylene carbonate and ethylene glycol, the absorbing solution contains water usually in a range of 1–30% by weight, preferably 3–15% by weight. Furthermore, when a homogeneous type catalyst is used as a carbonation catalyst, the catalyst is recycled as it is dissolved in the absorbing solution, and the content of the carbonation catalyst is usually 1–10% by weight, preferably 3–7 w % by weight of the whole absorbing solution.

As the melting point of ethylene carbonate is as high as 39° C., a low ethylene glycol blending ratio may result in solidification of the absorbing solution in a pipeline, when it is cooled to 50° C. or below, jeopardizing safe operation, but too much ethylene glycol lowers the absorption efficiency of ethylene oxide.

The temperature of the absorbing solution to be supplied is usually 10°–60° C., preferably 15°–40° C. from the view point of absorption efficiency. When a homogeneous type catalyst is dissolved in an absorbing solution and used as the carbonation catalyst, the carbonation catalyst contained in the absorbing solution is replenished via line 3 together with ethylene glycol, so that the loss caused by a discharge via line 17 to prevent heavy components from accumulating, is recovered to maintain the concentration. When a heterogeneous type carbonation catalyst is used, a part of ethylene glycol is drawn via line 17 by the discharge for the same reason, but the catalyst need not be replenished.

The absorption process of ethylene oxide is not particularly limited, but a counter-current contact type absorption column having high efficiency and little recovery loss is preferable. The form of the absorbing layer can be either a packed column type or a plate column type. In order to raise the absorption efficiency of ethylene oxide, the operating conditions of the absorption apparatus are preferably a high pressure and a low temperature; illustrative operating pressure is usually 5–40 kg/cm$^2$G (0.59–4.02 MPa), preferably 10–30 kg/cm$^2$G (1.08–3.04 MPa), and the operating temperature is usually 10°–80° C., preferably 15°–60° C. The gas/liquid ratio in moles is L/V of 0.1–2, preferably 0.2–1. By this absorbing procedure, substantially all the ethylene oxide in the gas resulting from the reaction and trace amounts of other co-existing gasses such as oxygen, ethylene, carbon dioxide, methane and ethane are absorbed in the liquid phase.

The remaining gas left after absorption/separation of ethylene oxide, i.e. a gas mainly containing oxygen, ethylene, carbon dioxide, methane and ethane, is drawn out via line 5, and a part or all of it is recycled to the reaction system of ethylene oxide as a feed gas or a diluting gas after the amount of the carbon dioxide contained therein is decreased by carbon dioxide removing treatment.

The absorbing solution having absorbed ethylene oxide is supplied to ethylene carbonate reactor via line 4. As the carbonation reactor, any reactor including a tubular type flow reactor and a vessel type batch reactor can be used. However, a tubular type flow reactor, in which a heat medium flows outside of the dual tube to allow the removal of the heat is preferable from the view point of the conversion rate of ethylene oxide, the removal of reaction heat, and continuous operation. The carbonation reaction is an exothermic reaction of 26 kcal/mole, and if the removal of the reaction heat is not properly done, an extraordinary rise in temperature may occur due to a runaway reaction to adversely effect the quality of the product. When a heterogeneous type solid catalyst is employed as the carbonation catalyst, the catalyst is packed in the reactor to form a layer, and the reaction is carried out.

(Carbonation step of ethylene oxide (step 2))

The carbonation catalyst used can be either a homogeneous type dissolved in the absorbing solution or a heterogeneous type comprising a packed layer of a solid catalyst. Illustrative examples of the homogeneous type carbonation catalyst include a bromide or iodide of an alkali metal (Japanese Patent Publication No. 38-23175), a halide of an alkaline earth metal (U.S. Pat. No. 2,667,497), an alkyl amine, a quaternary ammonium salt (U.S. Pat. No. 2,773,070), an organic tin, germanium or tellurium compound (Japanese Patent Laid-open No. 57-183784), and a halogenated organic phosphonium salt (Japanese Patent Laid-open No. 58-126884), and among them, a halide of an alkali metal such as potassium bromide and potassium iodide, and a halogenated organic phosphonium salt such as tributylmethylphosphonium iodide, tetrabutylphosphonium iodide, triphenylmethylphosphonium iodide, triphenylpropylphosphonium bromide, triphenylbenzylphosphonium chloride are preferable from the view point of activity and selectivity. In the case of a heterogeneous catalyst, illustrative examples include such known substances as an anion exchange resin having a quaternary ammonium salt as an exchange group (Japanese Patent Laid-open No. 3-120270), a heteropolyacid based on an oxide of tungsten or an oxide of molybdenum and a salt thereof (Japanese Patent Laid-open No. 7-206847).

The absorbing operation is usually carried out at such low temperature as 10°–80° C., therefore the probability of the reaction taking place between the ethylene glycol in the absorbing solution and the absorbed ethylene oxide during the absorbing operation, to generate diethylene glycol or higher polyglycols, is very small, and it is possible to substantially control the generation of these by-products.

In the case of a homogeneous catalyst, it is sent to the next step, i.e. to the carbonation reactor II while it is present in the absorbing solution, and works there as a catalyst for the reaction between the ethylene oxide in the absorbing solution and carbon dioxide to convert the ethylene oxide to ethylene carbonate.

As the carbon dioxide used for the reaction, recycled carbon dioxide from the carbon dioxide recovery apparatus III is supplied via line 6 and carbon dioxide generated in the hydrolysis step is recycled and supplied via line 11. Also, fresh carbon dioxide is supplied via line 10. As the fresh carbon dioxide to be supplied via line 10, the carbon dioxide is separated from the recycling gas to the ethylene oxide reactor, which is left after absorbing ethylene oxide, and can be used without further treatment.

The total amount of the carbon dioxide supplied via each line is usually 0.1–12 times, preferably 0.3–10 times, particularly preferably 0.5–5 times the molar quantity of ethylene oxide in the absorbing solution. In order to carry out the reaction quickly, sufficient diffusion of the carbon dioxide into the solution must be carried out, thus the higher pressure is preferable for the reaction conditions, and carbonation reaction is carried out under a pressure of 1–50 kg/cm$^2$G (0.20–5.01 MPa), preferably 3–20 kg/cm$^2$G (0.40–2.06 MPa). The reaction is usually carried out at a temperature of 50°–200° C. at a low temperature, the reaction rate becomes low and the reaction time is prolonged, thus making the reactor larger and therefore uneconomical. On the other hand, at a high temperature, the heat of the reaction may not be removed in time which may cause a runaway reaction, and the high temperature reaction itself may impart bad effects on the quality of the produced ethylene glycol, i.e. it is desirable to carry out the reaction usually at 80°–150° C. The required retention time in the reactor depends on the reaction temperature. However it usually is 5–180 minutes, preferably 12–120 minutes.

In addition, in the carbonate step, the direct reaction of ethylene oxide to ethylene glycol can be carried out together with the carbonation reaction when the higher temperature and the lower pressure within the range of temperature and pressure mentioned above are employed as reaction conditions.

(Step for recovering carbon dioxide)

After the carbonate step of ethylene oxide, the absorbing solution (hereinafter simply referred to as a reaction solution, so that the absorbing solution prior to the carbonating step can be distinguished therefrom) which almost all amounts of ethylene oxide are consumed, is supplied via line 7 to the carbon dioxide recovery apparatus in order to separate unconsumed excess carbon dioxide.

The reaction solution supplied to the carbon dioxide recovery apparatus is flushed by lowering the pressure usually to 0–15 kg/cm$^2$G (0.10–1.57 MPa), preferably 0–4 kg/cm$^2$G (0.10–0.49 MPa), and unused carbon dioxide, as well as oxygen, ethylene, carbon dioxide, methane and ethane and the like which are absorbed in the absorbing step and are accompanying the reaction solution are separated into the gas phase.

The separated carbon dioxide gas is partly discharged via line 9 in order to avoid the accumulation of gasses such as oxygen, ethylene, carbon dioxide, methane and ethane, and the rest is recycled to the ethylene carbonate reactor IV via line 6. The carbon dioxide is consumed by the reaction but the carbon dioxide generated in the hydrolysis reactor is recycled via line 11 and the carbon dioxide lost by the discharge is replenished by the fresh carbon dioxide sent via line 10 and the supply of the carbon dioxide to the reactor is kept constant.

The major portion of the reaction solution left after the separation and recovery of the carbon dioxide is recycled to the absorption column and the rest is supplied to the hydrolytic reactor via line 8. The ratio of the flow rate a at which the reaction solution is recycled to the absorption column, to the flow rate b at which the reaction solution is sent to the hydrolytic reactor is defined as b/a=d/c, wherein c is the molar quantity of ethylene carbonate in the absorbing solution of line 4 and d is the molar quantity of newly produced ethylene carbonate. Accordingly, when the quantity of ethylene oxide in the reaction gas and the quantity of the absorbing solution remain the same, the operation at a higher ethylene carbonate concentration in the absorbing solution of line 4 results in a smaller amount of the reaction solution to be drawn out for the hydrolytic reaction step, i.e. the hydrolysis step, and the subsequent steps can be carried out on a smaller scale. The ratio of the reaction solution to be drawn out for the hydrolysis step is usually 1–40% of the total amount.

The reaction solution which is recycled as the absorbing solution to the absorption column, is added to the stream via line 18 consisting of ethylene glycol of amount required to keep the constant concentration of ethylene glycol in the reaction solution and the solution containing the catalyst through the hydrolytic reaction step, and then the losses of the catalyst and ethylene glycol caused by the discharge via line 17 are recovered by replenishing via line 3 so that the composition of the reaction solution is returned to that before the absorption procedure, and the reaction solution is usually cooled then supplied to the absorption column as the absorbing solution.

(Hydrolysis step of ethylene carbonate (Step 3))

The reaction solution mainly containing ethylene carbonate and ethylene glycol, drawn via line 8 is supplied to the hydrolytic reactor together with water. The water necessary for the hydrolysis comprises the water present in the mixed solution resulting from the oxidation reaction, the water recovered in the dehydration step and supplied via line 12, and fresh water supplied via line 13. The total amount of water must be at least equimolar to the ethylene carbonate in the drawn mixed solution. In practice, water 1–5 times, preferably 1–2 times molar quantity of ethylene carbonate is supplied to carry out the reaction smoothly.

When a homogeneous type halogenated organic phosphonium salt is used as a carbonation catalyst, the carbonation catalyst is effective as a catalyst to be used in the hydrolysis step, so it is not always necessary to replenish with fresh catalyst in this step. As the hydrolytic catalyst supplied when necessary via line 13, a basic substance including a hydroxide of an alkali metal or alkaline earth metal such as sodium hydroxide, potassium hydroxide, calcium hydroxide, and magnesium hydroxide, a carbonate of an alkali metal such as sodium carbonate, potassium carbonate, and amines such as triethylamine, tributylamine and triisopropylamine, can be used, or a solid catalyst such as alumina and an inorganic ion exchanger can be packed in a reactor and used.

The reaction temperature is usually 100°–250° C., preferably 120°–180° C. from the view point of the reaction rate. It is desirable that the pressure not be too high to remove the generating carbon dioxide smoothly into the gas phase, and usually it is 0–10 kg/cm$^2$G (0.10–1.08 MPa), preferably 0–5 kg/cm$^2$G (0.10–0.59 MPa). The reaction time depends on the reaction temperature and the catalyst used, however, it must be within 5–240 minutes, preferably 10–180 minutes.

(Ethylene glycol recovery step)

After the hydrolysis is completed, the reaction solution is sent to a separation step wherein the excess water which is not consumed by the reaction, produced ethylene glycol and the catalyst when a homogeneous type catalyst is used are separated respectively. The details of the separation step differ according to the order of the separation, and for example, it is possible to structure the process wherein the separation of the catalyst takes precedence. However, the order of the separation of each component does not affect the constitution of the process as a whole. Here, a process will be described in which the separation of water takes precedence, and the produced ethylene glycol and the catalyst are then separated.

All of the reaction solution obtained after completion of the hydrolysis is introduced to a carbon dioxide separator V, wherein the pressure is lowered to 0–4 kg/cm$^2$G (0.10–0.49 MPa), and the carbon dioxide resulting from the hydrolysis is separated into a gas phase. The separated carbon dioxide is recycled to the carbonation reaction system via line 11.

The reaction solution after the separation of the carbon dioxide is introduced to the dehydration column VI via line 14. In the dehydration column, excess water which is not consumed in the hydrolysis reaction is separated through the top of the column. The separated water is directly stripped via line 19, although it is possible to recycle a part or all of the water to the hydrolytic reactor via line 12.

The solution at the bottom of the column is introduced to the ethylene glycol recovery column VII via line 15. The solution at the bottom of the dehydration column contains ethylene glycol and a trace amount of diethylene glycol as well as a catalyst when a homogeneous type catalyst is used. In the ethylene glycol recovery column, the purified ethylene glycol is recovered through the top of the column and all of the by-produced diethylene glycol as well as ethylene glycol containing a high concentration of the catalyst, when a homogeneous type catalyst is used, are recovered through the bottom of the column. The solution recovered through the bottom of the column is added to line 2 and recycled, after a part of it is discharged via line 17 in order to avoid accumulation of heavy components such as diethylene glycol.

The ethylene glycol obtained through the top of the column is drawn via line 16 and used as the product without any further treatment. However, it is possible to purify it further by conventionally employed processes such as distillation.

EXAMPLES

To further illustrate the present invention, the following examples are given, but they are not to be construed as limiting the present invention.

Example 1

(1) Absorption of Ethylene Oxide

A gas having a temperature of 30° C., obtained by oxidation of ethylene, containing 3 mol % of ethylene oxide was introduced at the rate of 15 kg/hour through the bottom of a counter flow catalyst packed absorption column having 30 stages (operation pressure: 14 kg/cm$^2$G (1.47 MPa) and a mixed solution of ethylene carbonate and ethylene glycol (mixed at 50:50 by weight) containing 5% by weight of tributylmethylphosphonium iodide as a catalyst and 3.8% by weight of water, was made to flow down from the top of the column at 30 kg/hour at 30° C. as an absorbing solution, and the ethylene oxide in the gas was absorbed in the solution. As a result of the analysis of the effluent, the ethylene oxide concentration in the gas at the top of the column was found to be 100 ppm and the absorption efficiency of the ethylene oxide was found to be 99% or more.

(2) Ethylene Carbonate Conversion Reaction

Carbon dioxide was mixed at 20 moles/hour with the mixed solution having absorbed ethylene oxide in (1) and it was supplied to a tubular type flow reactor (10 reaction tubes having a diameter of 3 cm, a length of 200 cm and retention time of 30 minutes). This was then heated to 100° C. using an external heat medium, so that the ethylene oxide in the absorbing solution was allowed to react with carbon dioxide and converted into ethylene carbonate. The conversion rate of the ethylene oxide at the outlet of the reactor was 99% or more and only a trace amount of diethylene glycol was produced as a by-product and no heavy components were found to be generated.

(3) Removal of Unreacted Carbon Dioxide Gas

The ethylene carbonate/ethylene glycol mixed solution produced in (2) was flushed at 100° C., 1 kg/cm$^2$G (0.20 MPa) so that the carbon dioxide in the mixed solution was removed. The carbon dioxide concentration in the mixed solution after the removal procedure was 0.1% by weight or less and the carbon dioxide removal rate was 90% or more.

(4) Hydrolytic Reaction

About 10% by weight of the mixed solution after the removal of the carbon dioxide was split and water was added at 400 g/hour (1.2 times the molar quantity of ethylene carbonate contained in the mixed solution) and supplied to a hydrolytic reactor (8 reaction tubes having a diameter of 3 cm, a length of 120 cm, retention time of 120 minutes). This was then heated to 150° C. using an external heat medium to carry out the hydrolytic reaction. The ethylene carbonate conversion rate at the outlet of the reactor was nearly 100%, the selectivity of ethylene glycol was 99% or more. The diethylene glycol was produced in an amount of 1% or less and no heavy components were found to be generated.

(5) Recovery of the Reaction Product

Carbon dioxide was removed from the reaction mixture containing the catalyst obtained in (4) by a gas/liquid separator and the resulting liquid phase was subjected to vacuum distillation in a dehydration column having 15 stages to remove the water from the reaction mixture. Then the liquid at the bottom of the column was further subjected to the vacuum distillation and purified ethylene glycol was obtained through the top of the column at a constant rate of 980 g/hour. Ethylene glycol containing the catalyst in a high concentration was drawn out through the bottom of the column.

(6) Recycling of the Absorbing Solution

90% by weight of the mixed solution left after the removal of the carbon dioxide was cooled to 30° C. and recycled to the absorption column as an absorbing solution. The ethylene glycol containing the catalyst of high concentration obtained in (5) was discharged at 160 g/hour and the rest was recycled as a part of the absorbing solution after the catalyst was replenished. The recycling of carbon dioxide via line 6 and line 11 and recycling of water via line 12 shown in the FIGURE were not carried out and fresh carbon dioxide and fresh water were supplied.

The above-mentioned recycling system was constructed and an experiment was carried out for 3 consecutive weeks. However, no loss of ethylene oxide, lowering of selectivity, generation or accumulation of heavy components were observed, and stabilized operation could be carried out.

According to the present invention, a large energy consuming step such as releasing of ethylene oxide and separation of excess amounts of water during the ethylene glycol production becomes unnecessary and the process can be greatly simplified by combining the ethylene oxide absorption step and the carbonation step.

What is claimed is:

1. A process for producing ethylene glycol from ethylene oxide without employing a scrubbing or stripping ethylene oxide step, comprising the steps of:

a. directly absorbing ethylene oxide in a gas formed by oxidation of ethylene in an absorbing solution mainly containing ethylene carbonate and ethylene glycol without scrubbing and stripping ethylene oxide, b. reacting the ethylene oxide in the absorbing solution with carbon dioxide in the presence of a carbonation catalyst to convert ethylene oxide to ethylene carbonate, c. subjecting a part of ethylene carbonate to hydrolysis in the presence of a hydrolytic catalyst to form a hydrolysate containing ethylene glycol and allowing the remaining ethylene carbonate to recycle as the absorbing solution, and d. recovering the ethylene glycol from the hydrolysate by distillation.

2. A process for producing ethylene glycol according to claim 1, further comprising recovering the unreacted carbon dioxide after step b.

3. A process for producing ethylene glycol according to claim 1, wherein the total amount of the ethylene carbonate and the ethylene glycol contained in the absorbing solution used in step a is not less than 50% by weight of the absorbing solution.

4. A process for producing ethylene glycol according to claim 1, wherein the weight ratio of the ethylene glycol to the ethylene carbonate is 0.1–9.

5. A process for producing ethylene glycol according to claim 1, wherein the absorbing solution mainly contains ethylene carbonate, ethylene glycol and water.

6. A process for producing ethylene glycol according to claim 1, wherein the gas resulting from the oxidation of ethylene contains 0.5–5 mol % of ethylene oxide.

7. A process for producing ethylene glycol according to claim 5, wherein the amount of water contained in the absorbing solution used in step a is 1–30% by weight of the absorbing solution.

8. A process for producing ethylene glycol according to claim 1, wherein the absorption of ethylene oxide is carried out at a temperature of 10°–80° C. in step a.

9. A process for producing ethylene glycol according to claim 1, wherein the carbonation catalyst is a halogenated organic phosphonium salt.

* * * * *